United States Patent
Horne et al.

(10) Patent No.: US 7,536,220 B2
(45) Date of Patent: May 19, 2009

(54) METHODS FOR OBTAINING QUICK, REPEATABLE AND NON-INVASIVE BIOELECTRICAL SIGNALS IN LIVING ORGANISMS

(75) Inventors: Douglas S. Horne, Murray, UT (US); Phillip Dietz, St. George, UT (US); Harold E. Swift, Lehi, UT (US)

(73) Assignee: BioMeridian International, Inc., Bluffdale, UT (US)

( * ) Notice: Subject to any disclaimer, the term of this patent is extended or adjusted under 35 U.S.C. 154(b) by 0 days.

(21) Appl. No.: 11/944,696

(22) Filed: Nov. 26, 2007

(65) Prior Publication Data

US 2008/0071188 A1    Mar. 20, 2008

Related U.S. Application Data

(62) Division of application No. 10/621,178, filed on Jul. 16, 2003.

(51) Int. Cl.
*A61B 5/05* (2006.01)
*A61H 39/02* (2006.01)

(52) U.S. Cl. ........................ 600/547; 600/548

(58) Field of Classification Search ................. 600/547, 600/548
See application file for complete search history.

(56) References Cited

U.S. PATENT DOCUMENTS

| | | | | |
|---|---|---|---|---|
| 2,684,670 A | * | 7/1954 | Mathison | 600/547 |
| 3,508,540 A | * | 4/1970 | Cavallari, Jr. et al. | 600/547 |
| 3,784,908 A | * | 1/1974 | Anderson | 600/547 |
| 3,894,532 A | * | 7/1975 | Morey | 600/547 |
| 3,980,073 A | * | 9/1976 | Shaw, IV | 600/547 |
| 4,016,870 A | * | 4/1977 | Lock | 600/548 |
| 4,052,978 A | * | 10/1977 | Eugenio | 600/548 |
| 4,088,125 A | * | 5/1978 | Forgione et al. | 600/547 |
| 4,096,582 A | * | 6/1978 | Bailey et al. | 365/13 |
| 4,408,617 A | * | 10/1983 | Auguste | 600/548 |
| 4,832,036 A | * | 5/1989 | Cartmell | 600/396 |
| 4,940,060 A | * | 7/1990 | Gu et al. | 600/548 |
| 4,947,862 A | * | 8/1990 | Kelly | 600/547 |

(Continued)

OTHER PUBLICATIONS

BioMeridian International, News Releases Webpage, Jan. 20, 2002, (http:llweb.archive.orglweb1200202120412221www.biomeridian.comldefault.db.htm).*

(Continued)

*Primary Examiner*—Max Hindenburg
*Assistant Examiner*—Jeffrey G Hoekstra
(74) *Attorney, Agent, or Firm*—Michael F. Krieger; Kirton & McConkie

(57) ABSTRACT

The present invention is a method for obtaining an electrical signal from a patient that corresponds to a meridian. The present method contemplates locating a dermal area of a patient proximate a meridian. One embodiment of the present invention comprises locating a dermal area by iteratively measuring and comparing the conductivity of a patient's skin until a significant level of conductance is indicated. A probe may then be placed in contact with the dermal area, and actuated to obtain an electrical signal therefrom. The probe tip may be specially designed to apply an appropriate amount of pressure to the dermal area to directly sense a meridian, and configured to avoid erroneous measurements resulting from misalignment of the probe or probe tip.

12 Claims, 14 Drawing Sheets

U.S. PATENT DOCUMENTS

| | | | | |
|---|---|---|---|---|
| 5,001,436 | A * | 3/1991 | Scot et al. | 324/689 |
| 5,012,816 | A * | 5/1991 | Lederer | 600/548 |
| 5,024,236 | A * | 6/1991 | Shapiro | 600/548 |
| 5,205,330 | A * | 4/1993 | Sekine | 141/59 |
| 5,339,827 | A * | 8/1994 | Masopust | 600/548 |
| 5,409,011 | A * | 4/1995 | Alexeev et al. | 600/547 |
| 5,588,440 | A * | 12/1996 | Cowie | 600/547 |
| 5,938,593 | A * | 8/1999 | Ouellette | 600/300 |
| 5,957,862 | A * | 9/1999 | Lu et al. | 600/548 |
| 5,961,471 | A * | 10/1999 | Nickson | 600/546 |
| 6,004,312 | A * | 12/1999 | Finneran et al. | 600/546 |
| 6,026,322 | A * | 2/2000 | Korenman et al. | 600/547 |
| 6,067,468 | A * | 5/2000 | Korenman et al. | 600/547 |
| 6,285,905 | B1 * | 9/2001 | Chiang et al. | 607/2 |
| 6,299,586 | B1 * | 10/2001 | Cao | 601/134 |
| 6,306,160 | B1 * | 10/2001 | Nidetzky | 607/89 |
| 6,347,238 | B1 * | 2/2002 | Levengood et al. | 600/372 |
| 6,391,005 | B1 * | 5/2002 | Lum et al. | 604/117 |
| 6,392,362 | B1 * | 5/2002 | Ito | 315/224 |
| 6,480,735 | B2 * | 11/2002 | Colloca et al. | 600/546 |
| 6,788,966 | B2 * | 9/2004 | Kenan et al. | 600/372 |
| 2001/0034491 | A1 * | 10/2001 | Benson et al. | 600/547 |
| 2002/0151815 | A1 * | 10/2002 | Kawanishi et al. | 600/547 |
| 2002/0161312 | A1 * | 10/2002 | Campbell et al. | 600/547 |
| 2003/0055357 | A1 * | 3/2003 | Rentea | 600/547 |
| 2004/0133081 | A1 * | 7/2004 | Teller et al. | 600/300 |
| 2004/0204658 | A1 * | 10/2004 | Dietz et al. | 600/547 |
| 2005/0014999 | A1 * | 1/2005 | Rahe-Meyer | 600/323 |

OTHER PUBLICATIONS

Damijan Miklavcic et al., Electric properties of tissues, Wiley Encyclopedia of Biomedical Engineering, 2006, John Wiley & Sons, Inc. found at http://lbk.fe.uni-lj.si/pdfs/webt2OO6.pdf.*

NIH Consensus Statement Nov. 3-5 1997; 15(5):1-34, available at http://consensus.nih.gov/1997/1997acupuncture107html.htm.*

* cited by examiner

METHODS FOR OBTAINING QUICK, REPEATABLE AND NON-INVASIVE BIOELECTRICAL SIGNALS IN LIVING ORGANISMS

CROSS-REFERENCE TO RELATED APPLICATIONS

This application is a divisional of prior application Ser. No. 10/621,178, filed Jul. 16, 2003.

BACKGROUND OF THE INVENTION

1. Field of the Invention

The present invention relates to a method for obtaining electrical signals from a patient to assess a medical condition. In particular, the present invention relates to a method for accurately locating a meridian transdermally and obtaining a value for an electrical attribute corresponding to such a meridian.

2. Background and Related Art

Traditional medical science has long recognized certain electrical characteristics of humans and other living organisms. For example, the traditional medical community has recognized electrical potentials generated by the human body in such forms as brain waves, detected by electro-encephalographs (EEG), electrical impulses resulting from muscular heart activity, as detected by electrocardiograms (EKG), and other electrical potentials measurable at other areas of the human body. While the levels of electrical activity at sites on the human body are relatively small, such signals are nonetheless measurable and consistent across the species.

In addition to measurable currents, the human body and other mammalian organisms exhibit specific locations where a resistance value and, inversely, a conductance value are relatively predictable for healthy individuals. These locations, known as anatomical dermal conductance points, exhibit unique resistance values. Interestingly, such locations exhibit a resistive reading of approximately 100,000 ohms and coincide with the acupuncture points defined anciently by the Chinese.

Ancient Chinese medical practitioners treated many unfavorable health conditions by inserting thin needles into the body at specific points to pierce peripheral nerves, a technique commonly known as acupuncture. Acupressure is a gentle, noninvasive form of the ancient Chinese practice of acupuncture that implements thumb or finger pressure or electrical stimulation at these same points, also known as acupressure points, to provide similar results.

The representative acupressure points and their relationship with organs and life systems of the human body have been characterized into more than 800 points that are organized into approximately 12 basic meridians that run along each side of the body. Each pair of meridians corresponds to a specific organ or function such as stomach, liver, spleen/pancreas and lung. Acupressure points are named for the meridian they lie on, and each is given a number according to where along the meridian it falls. For example, Spleen 6 is the sixth point on the Spleen meridian. The measurable attributes of each acupressure point reflect the energetic condition of the inner organ or other functions of the human body corresponding to such point.

Acupressure points are generally located at the extremity region of the hands and feet. As introduced above, the resistance value of healthy tissue measured at an acupressure point is generally in the range of about 100,000 ohms. When conditions arise affecting higher conductivity readings, perhaps from inflammation or infection, the measured resistance value becomes less than 100,000 ohms. Likewise when conditions arise affecting lower conductivity readings, perhaps from tissue fatigue or a degenerative state, conductivity is reduced, causing the resistance value to be higher.

Systems have been implemented to measure a resistance, voltage, and/or current values at acupressure points located on a meridian and to present the values to a clinician for use in assessing a condition. Traditional systems, however, have proven difficult to use in pinpointing the precise location of such acupressure points, as required to effectively assess a medical condition. Indeed, most known systems require contacting an acupressure point with the probe tip placed with a specific amount of pressure at a specific angle to obtain a reliable electrical measurement for assessment use. Measurement inaccuracies result from the failure to precisely locate the probe tip on the acupressure point and properly apply the appropriate rate and amount of pressure to the probe tip. Furthermore, if too much or too little pressure is applied to the point or if the pressure is applied too slowly or too quickly the measured values will either be false high or low. Learning the proper techniques to obtain accurate readings can take months and even then some may not ever be able to acquire the skill necessary to respectively obtain accurate readings.

Accordingly, what is needed is a method for accurately applying the appropriate rate and amount of pressure to the probe tip and locating a meridian or acupressure point. Thus, making the learning process much shorter and measurements that are less as subject to user error.

SUMMARY OF THE INVENTION

The present invention is a method for obtaining measured electrical values from a patient that correspond to a meridian or acupressure point. The present method contemplates locating with a probe a dermal area of a patient proximate a meridian. Such dermal area may be located by iteratively measuring and comparing the conductivity of a patient's skin until a significant level of conductance is indicated, thus suggesting the proximity of a meridian or acupressure point. An isolation hood at the end of the probe is then held in contact with the dermal area, and the probe tip is directed toward the skin by a motor actuated to obtain an electrical signal therefrom. The probe tip is specially designed with a motor and logic feedback loop to apply an appropriate amount of pressure to the dermal area to accurately measure the signal at a meridian.

An object of some embodiments of the present invention is to provide a method for obtaining a consistent and repeatable electrical signal from a dermal area corresponding to a meridian. Such signals are obtained by controlling the rate and amount of pressure applied to the probe tip.

Another object of some embodiments of the present invention is varying the rate and amount of pressure via a feed back loop that allows the rate and pressure to compensate for individual variances in skin thickness, moisture content, and such like.

A further object of some embodiments of the present invention is to provide a reliable method for obtaining an electrical signal from a patient that does not require implementation by an experienced or highly skilled professional.

Yet another object of some embodiments of the present invention is to provide a method for obtaining an electrical signal from a patient that enables fast and accurate results.

These and other features and advantages of the present invention will be set forth or will become more fully apparent in the description that follows and in the appended claims.

The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE INVENTION

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The following disclosure of the present invention is grouped into two subheadings, namely "Obtaining Quick and Repeatable Electrical Signals" and "Utilizing Electrical Feedback." The utilization of the subheadings is for convenience of the reader only and is not to be construed as limiting in any sense.

Obtaining Quick and Repeatable Electrical Signals

The present invention relates to a method for obtaining electrical signals from a patient to assess a medical condition. In particular, the present invention relates to a method for accurately locating a meridian transdermally and obtaining a value for an electrical attribute corresponding to such a meridian.

As used in this specification, the term "meridian" refers to an electrical pathway or energy channel along the body, wherein each meridian contains at least one acupressure point corresponding to at least one organ or system within the body. The term "dermal area" refers to a portion of a patient's skin located near a meridian. The term "conductance" or "conductance value" refers to a rate of electrical potential initiated at one point and measured at a second point, wherein the second point corresponds to a dermal area. The term "meridian signal" refers to a reading or measurement detected or taken at a dermal area that indicates a conductance value and or a voltage potential and or another type of reading or signal that assesses a meridians condition.

Figure 1:
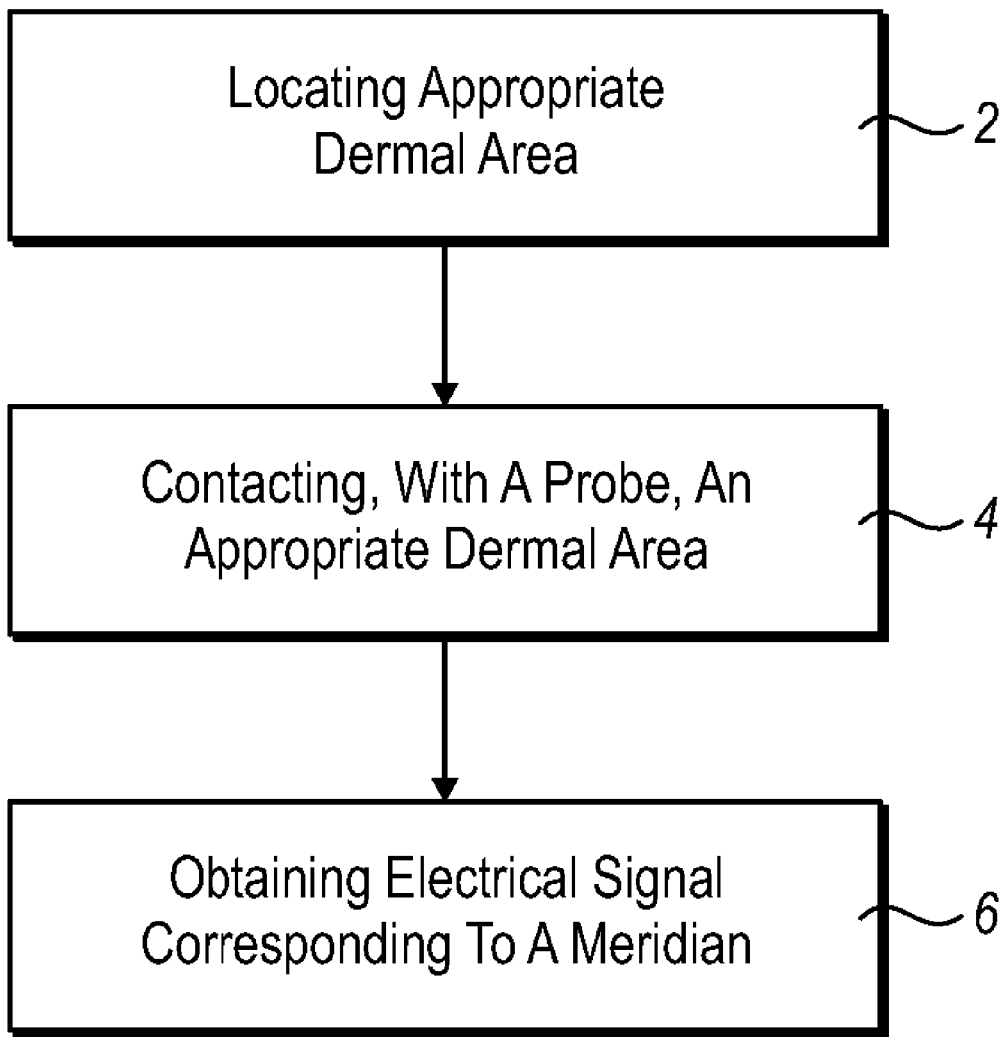
FIG. 1 is a flow chart illustrating a method for obtaining an electrical signal from a patient in accordance with the present invention.

Referring to FIG. 1, the method of the present invention may comprise first locating a dermal area corresponding to a meridian (2). A dermal area corresponding to a meridian may be approximated by analyzing a point location chart and then attempting to locate the same dermal area on a patient. This method, though available, is not preferred due to its subjectivity and potential for error. Alternatively, a meridian may be located by introducing an electrical signal at one point and measuring the resulting meridian signal at a second point to determine conductivity or resistivity. A dermal area corresponding to a meridian exhibits higher conductivity and, hence, lower resistivity, than adjacent, non-meridian containing dermal areas. A relatively high conductance value, or low resistance value, may then be used to more accurately isolate a dermal area corresponding to a meridian. This aspect of locating a dermal area corresponding to a meridian 2 is discussed in more detail with reference to FIG. 2 below.

A second step of the present method may comprise contacting, with a probe, an appropriate dermal area 4. Contacting an appropriate dermal area 4 entails approximating the location of a meridian, applying the probe to the skin in that area, checking the signal and comparing that signal to the original at a new location, and then stopping at the location with the best signal. Some embodiments have a sensor and logic to quickly locate the points that are closest to the meridian. After locating the meridian, the isolation hood is aligned with the meridian to ensure accurate readings of meridian signals corresponding thereto. Traditionally, application of pressure to and alignment of the probe have been highly subjective processes, with accurate results dependent primarily on the skill of the practitioner. Indeed, the historical lack of physical means for quantitative detection and evaluation of meridian characteristics has seriously limited their availability and application in medicine. As a result, one aspect of the present invention is directed to implementing a probe having physical qualities capable of objectively detecting and analyzing electrical signals corresponding to a meridian. This aspect of the present invention is discussed in more detail with reference to FIGS. 5*a* and 5*b* below.

Figure 5A:
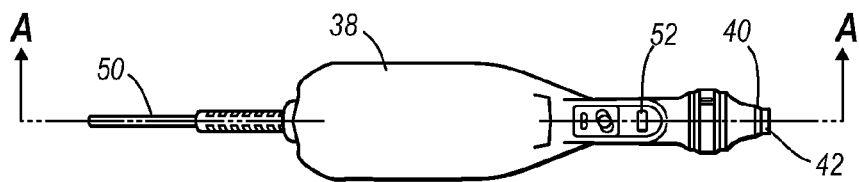
FIGS. 5A-5C illustrate a representative embodiment of a probe as disclosed herein.
Figure 5B:
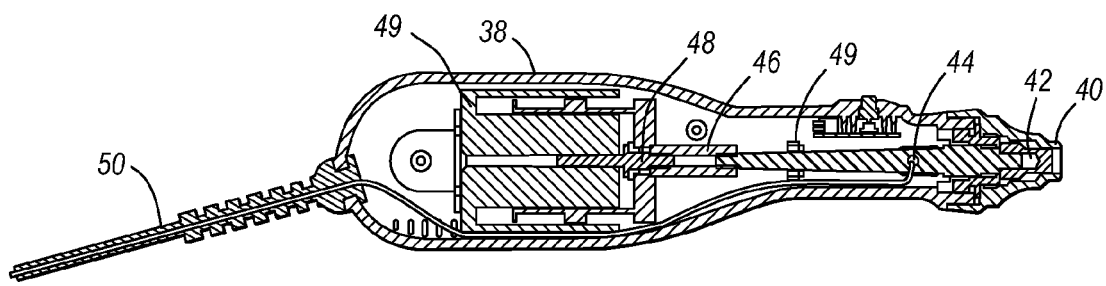
Figure 5C:
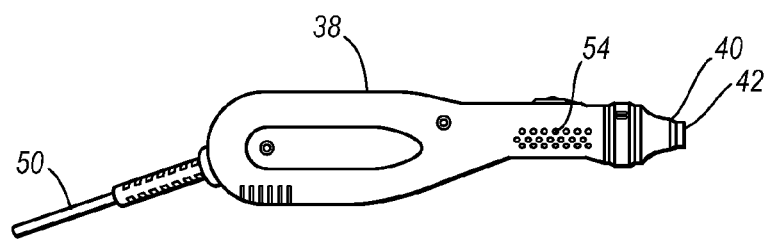

A third step of the present method may comprise obtaining a meridian signal from a probe 6 (FIG. 5C). An electrical signal may comprise a conductance value or a resistance value corresponding to the dermal area. Where a conductance value is obtained from a probe, a meridian may be located where the conductance value is significantly greater than an adjacent dermal area. On the other hand, where a resistance value is obtained, a resistive value significantly less than an adjacent dermal area may indicate a location of a meridian.

Figure 2:
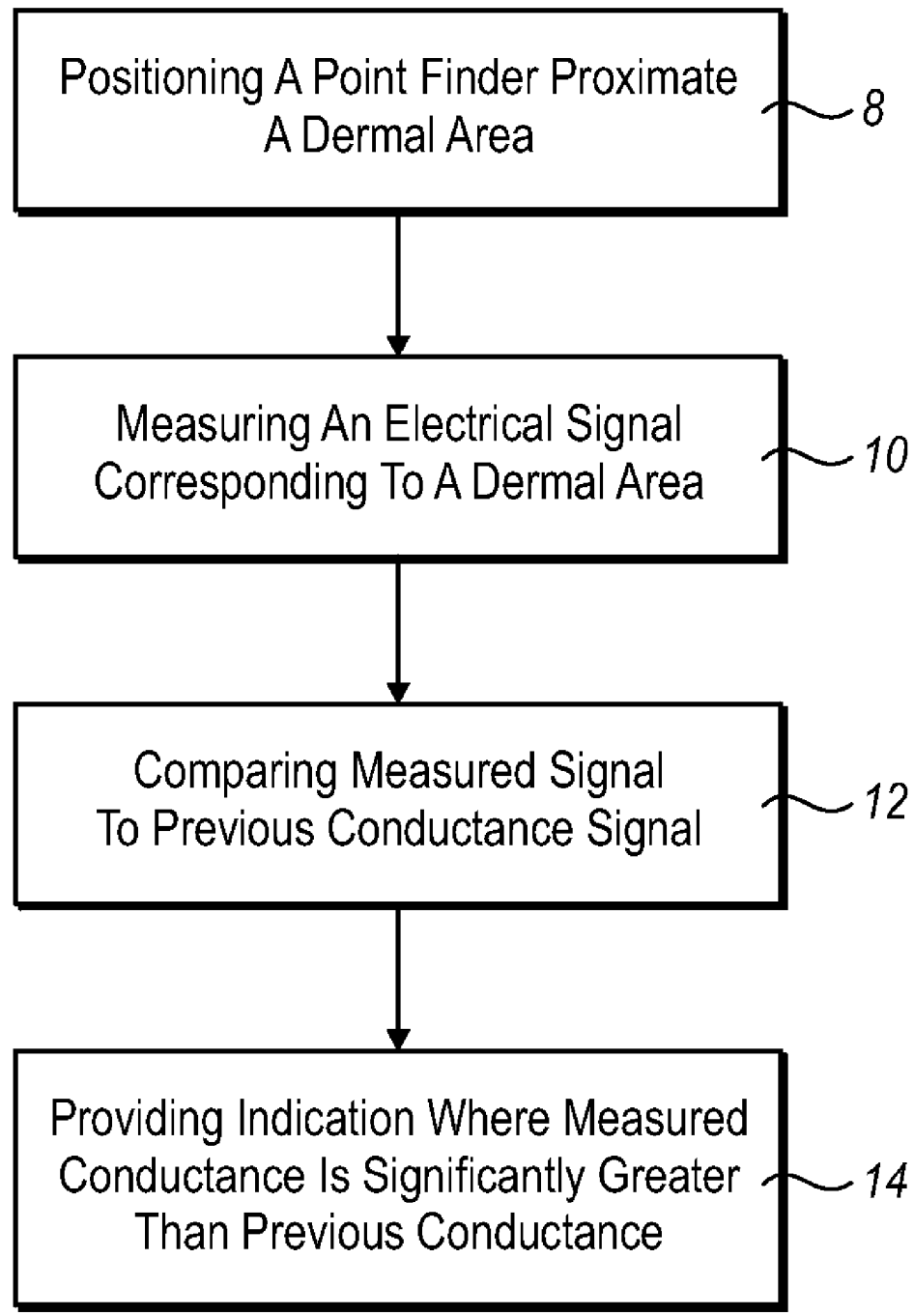
FIG. 2 is a detailed flow chart illustrating various steps that may be followed when locating a dermal area in accordance with the present invention.
Figure 3:
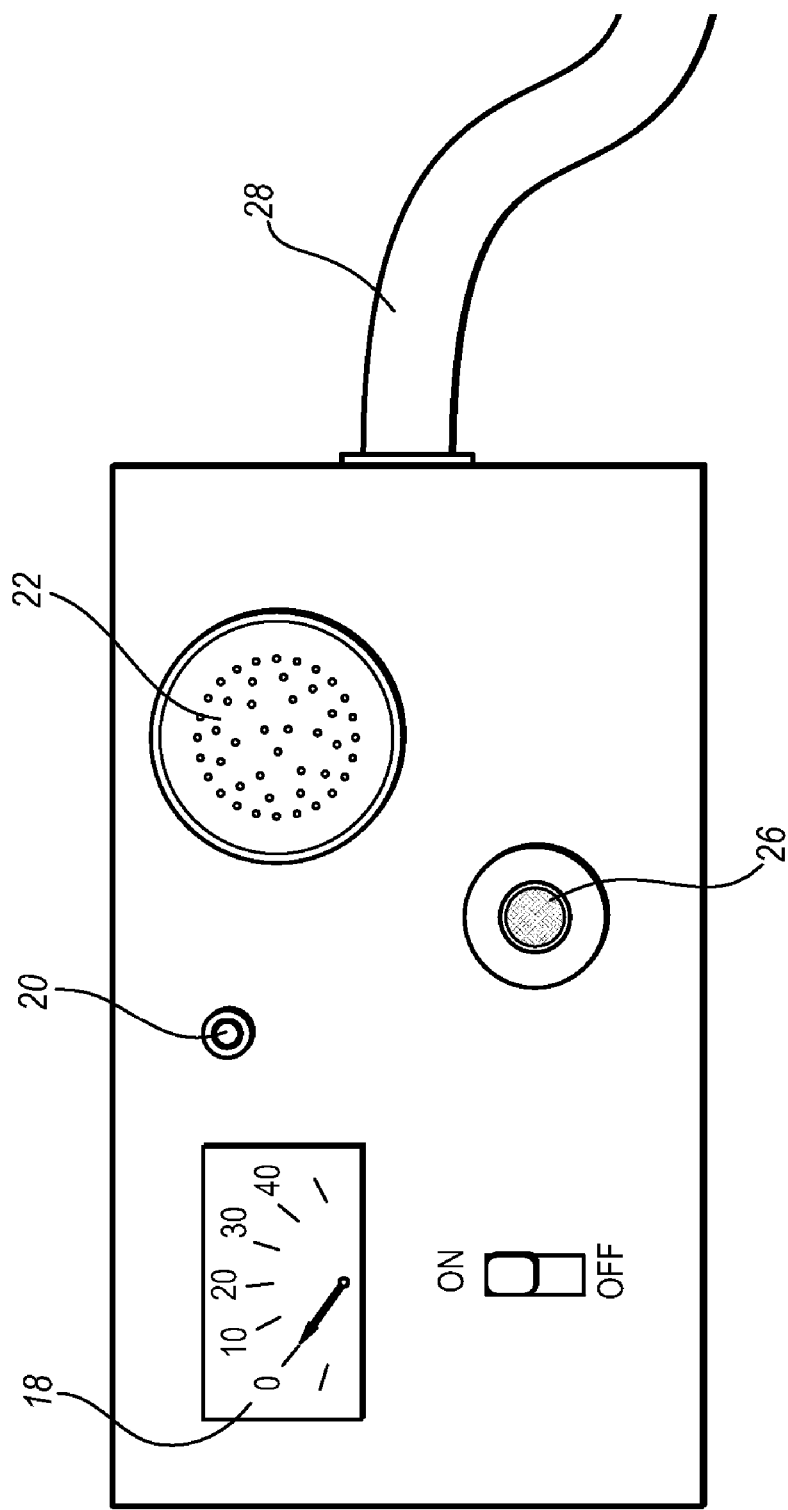
FIG. 3 illustrates one embodiment of a point locator as disclosed herein.

Referring now to FIG. 2, locating a dermal area corresponding to a meridian 2 entails positioning a point finder proximate a dermal area 8. Positioning a probe proximate a dermal area 8 may comprise direct or indirect contact between a dermal area and a point finder. Indirect contact between a dermal area and a point finder may be achieved by, for example, applying a medium to the dermal area prior to contacting the area with a point finder to facilitate in hydrating the cornified layer of the epidermis without having to use the usual pressure required to accomplish this as is done during point reading. Alternatively, positioning a point finder proximate a dermal area 4 may comprise no contact whatsoever between the point finder and the dermal area, so long as the point finder may sense a meridian signal corresponding to the dermal area.

Second, locating a dermal area corresponding to a meridian 2 may comprise measuring an electrical signal corresponding to a dermal area 10 and comparing the measured signal to a previously received signal 12. If a measured signal substantially differs from a previously received signal in a manner associated with locating a meridian, a point finder may provide an audible, visual or tactile indication 14, or a combination of indications, to so indicate. For example, if a measured electrical signal is a conductance value that is substantially higher than a previously received conductance value, the point finder may produce an audible, visual, tactile or combination indication. Similarly, if a measured electrical value is a resistance value that is substantially less than a previously received resistance value corresponding to an adjacent dermal area, a point finder may so indicate. In this manner, a dermal area corresponding to a meridian may be isolated as a focus point for more precisely locating and evaluating a meridian.

Figure 4:
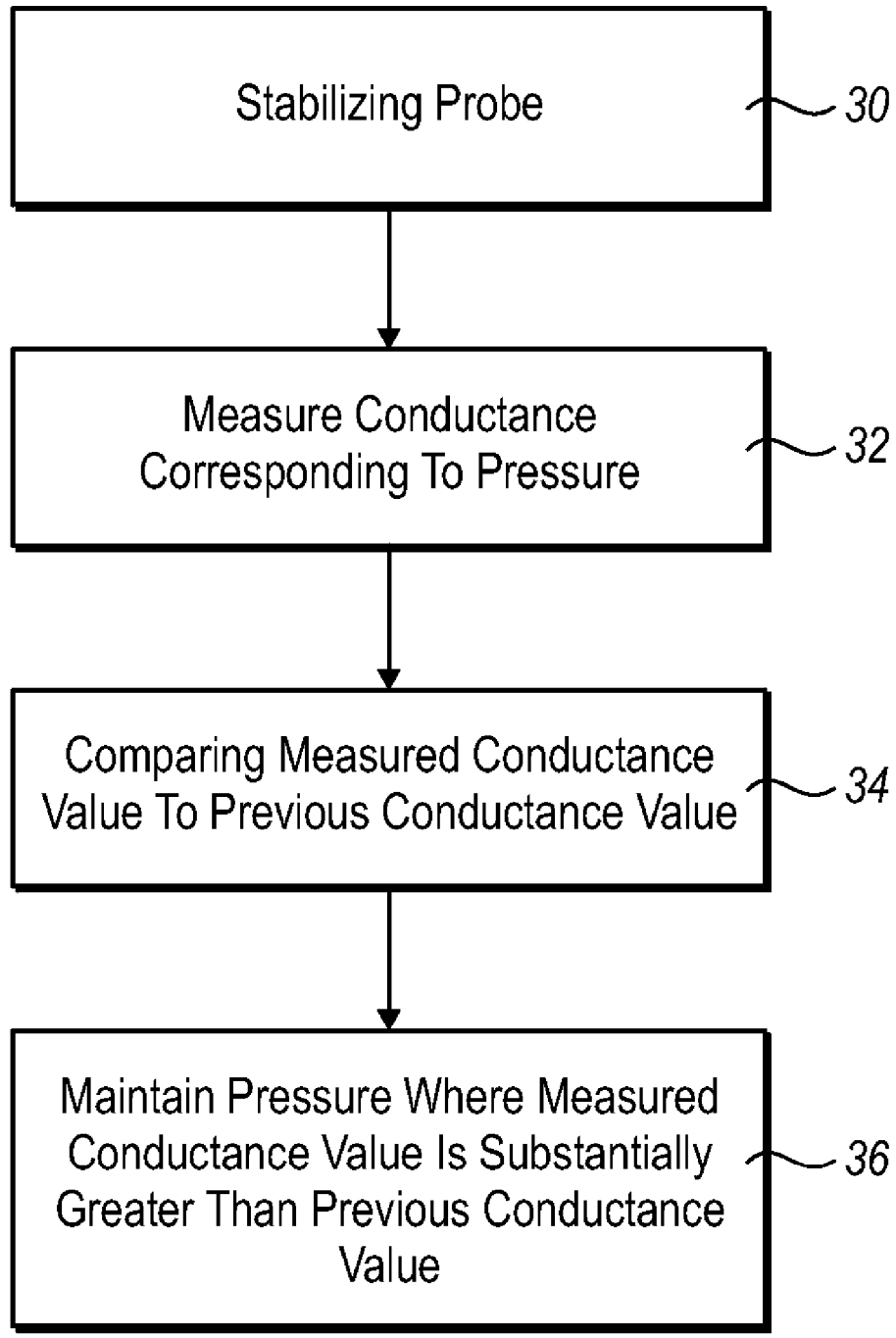
FIG. 4 is a detailed flow chart illustrating various steps that may be followed when contacting a dermal area with a probe in accordance with the present invention.

Referring to FIG. 2, FIG. 4, and FIG. 5B obtaining an electrical signal 6 entails stabilizing a probe against a patient's skin 30 by way of, for example, a stabilizing and isolating device attached to the probe, such as the isolation hood 40. A stabilizing device may comprise prongs or a cylinder or other substantially rigid member coupled to or integrated with the probe such that the stabilizing device is maintained in a fixed position relative to a patient's skin. Another function of the stabilizing device is to isolate the manually affixed portion of the probe from the probe tip such that a meridian signal is not influenced with unwanted input.

After measuring a conductance value corresponding to an amount of pressure 32 and iteratively comparing the measured conductance value to a previously obtained conductance value corresponding to a previously applied amount of pressure 34 to determine a relationship between the two conductance values, a motor is activated and the tip 42 descends through the isolation hood to apply more pressure. When the measured conductance value is substantially greater than the previously obtained conductance value, the amount of pressure corresponding to the measured conductance value may be maintained 36 and a meridian signal obtained there from 6.

Referring to FIGS. 5A and 5B and FIG. 6C, certain embodiments of the present methods may be achieved by providing, for example, a probe apparatus comprising a probe housing 38 having a probe tip 42 and a isolation hood 40. The isolation hood 40 may comprise a cylinder coupled to or integrated with the probe housing 38 such that the isolation hood 40 is functionally discrete from the probe tip 42. In this manner, pressure applied to the isolation hood 40 does not affect pressure applied to the probe tip 42. In fact, the cylindrical structure of the isolation hood 40 allows the probe tip 42 to independently slide through the isolation hood 40. The isolation hood 40 thus ensures that an electrical signal obtained by the probe tip 42 is objective and repeatable by preventing untoward manipulation of the probe apparatus to achieve a particular electrical signal.

Figure 6:
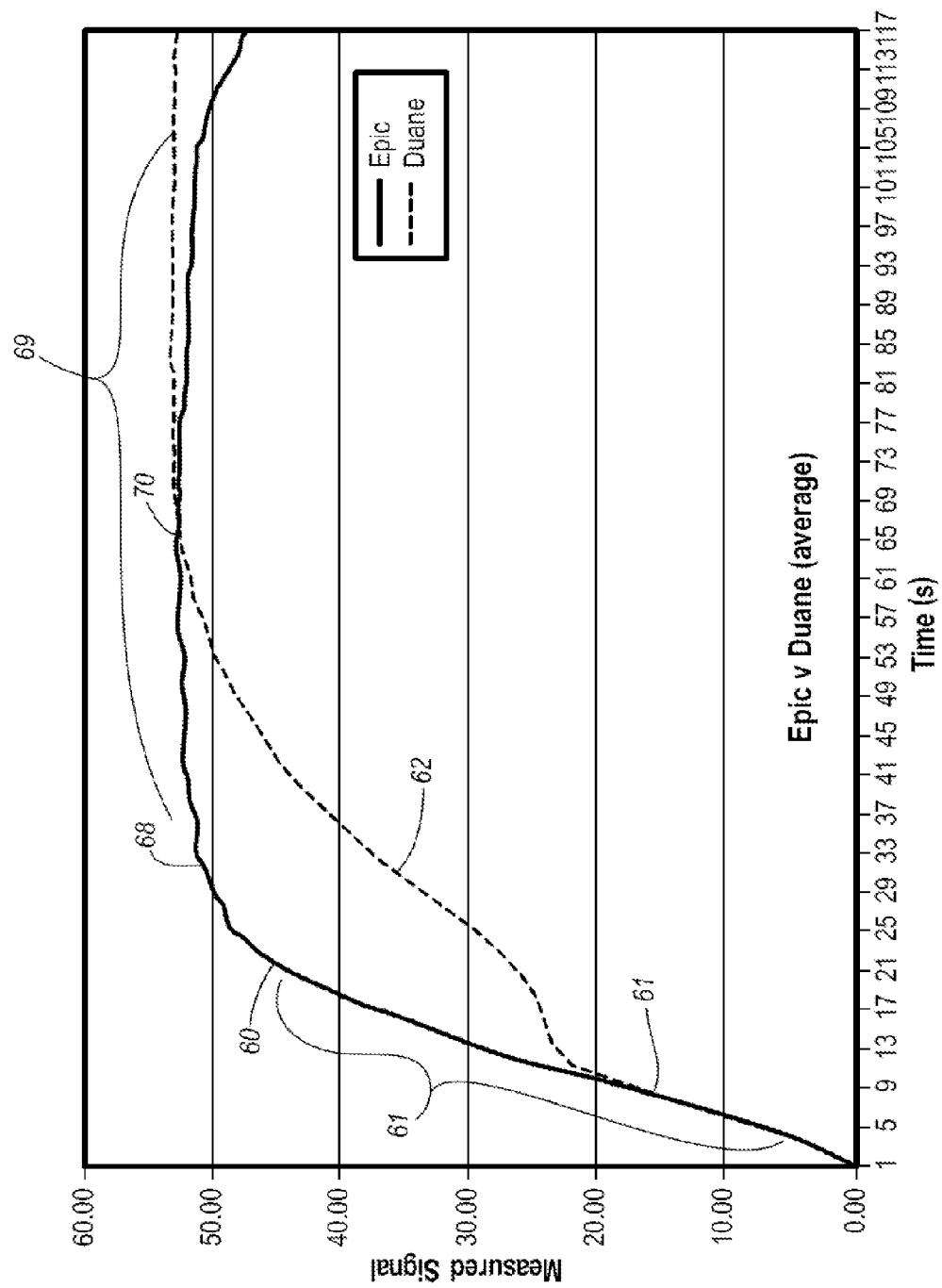
FIG. 6 is a comparative graphical representation illustrating the efficiency and consistency of the present method ("Epic" in the legend) in obtaining an electrical signal compared to the prior art ("Duane" in the legend)
Figure 14:
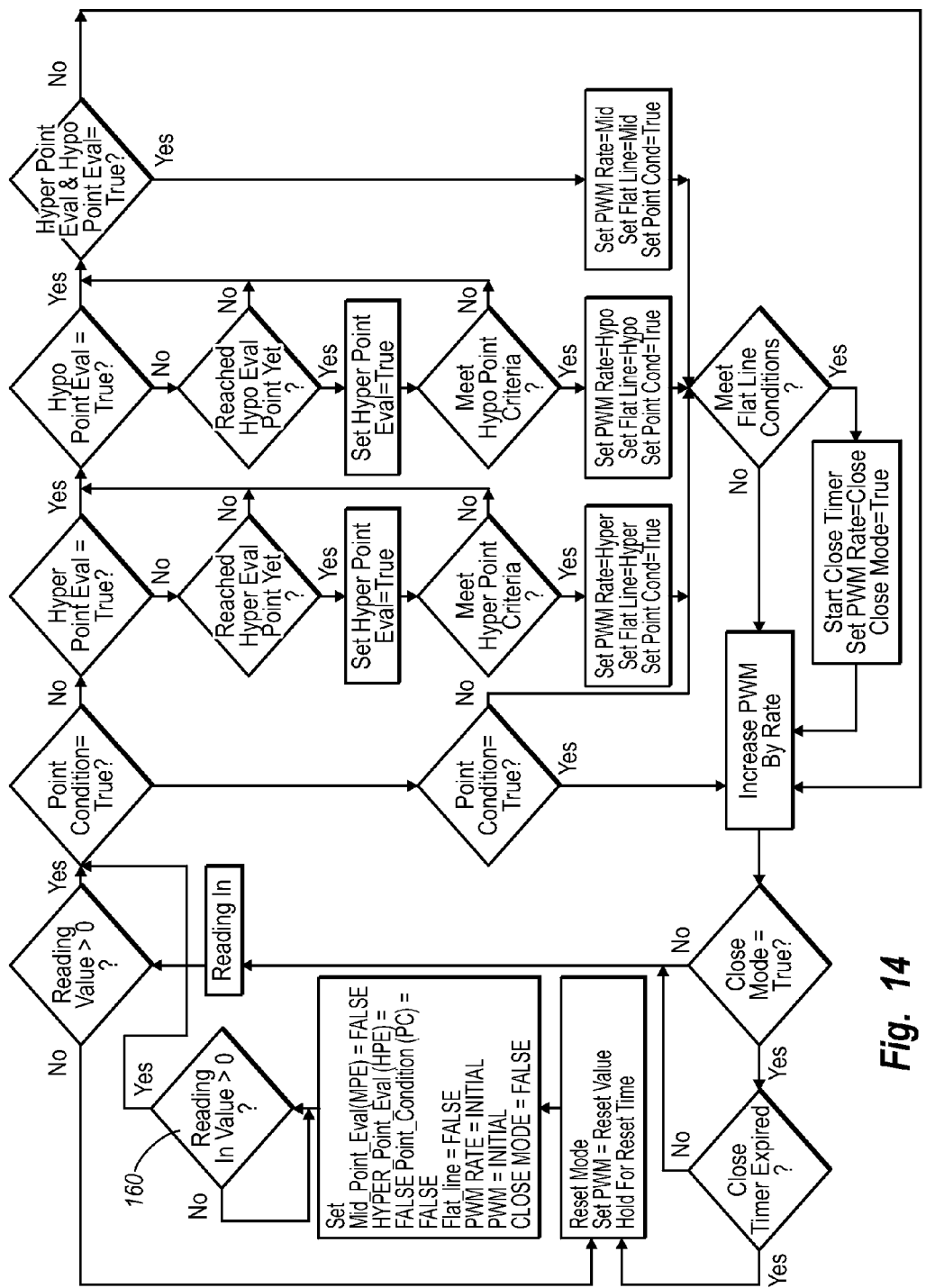
FIG. 14 is a flow chart that illustrates a representative embodiment for providing feedback in obtaining quick and repeatable electrical signals.

A probe apparatus may further comprise a probe tip 42 and detector 44 coupled to an isolator 46 which is coupled to and insulated from the biasing element 48, which is all enclosed in the probe housing 38. One end 49 of the biasing element 48 alone is coupled to the probe housing 38 while the probe apparatus moves freely within the probe housing 38 and the end 49 of the biasing element 48. The probe tip 42 is operably connected to a feedback loop 42. 44. 5-. 11-. FIG 14 and 49 which comprises, for example, hardware, electronics, firmware and software. A portion of the feedback loop 32, 34, and 36 and shown in more detail in FIG 14 may compare a first detected meridian signal to a second detected meridian signal and compare the relationship between the first and second detected meridian signals to compute and adjust the input that drives the biasing element 48. A biasing element 48 may comprise any mechanical, pneumatic, hydraulic, electrical or magnetic mechanism, or any other mechanism known to those in the art, by which to vary the pressure applied to a probe apparatus and ultimately to the probe tip 42. The feedback loop may compute information received from meridian signals and adjusts the amount of pressure applied to the probe tip 42 by the biasing element 48 accordingly. For example, if a measured conductance value corresponding to a present pressure is slightly greater than the previous measured conductance value received from a previous smaller pressure, then the feedback loop will evaluated such information and may actuate the biasing element to apply slightly more pressure to the probe tip 42 to obtain a future conductance value. The relationship of the change in meridian signal relative to the change in applied pressure is termed; the "sensitivity value". The computer in the feedback loop will maintain this progressive process of incrementally driving the biasing element 48 with slightly more pressure as long as the sensitivity values are linear 61 (FIG. 6). If, however, the feedback loop senses a definite change in the slope of the sensitivity values 60 then the feedback loop may determine to intelligently moderate 68 the pressure applied to the probe tip 42 so that the slope of the sensitivity values may become relatively horizontal 69.

The probe apparatus may comprise an automatic reset initiated after the feedback loop has determined the reading cycle is complete, thus preparing it for its next reading. This process may consist of an automated sequence of events including: retracting the detector 44, holding it in its retracted position so that the probe tip 42 is no longer in contact with the skin for an adjustable amount of time, extend the detector 44, and holding the detector in its extended position with an adjustable amount of pressure until the feedback loop influences it otherwise.

The probe apparatus may also comprise an automatic reading initiator. This initiator may be triggered when the feedback loop senses a feedback signal. The feedback signal may be a conductance value greater than 0. This initiator may be comprised of an automated sequence of events including: retracting the probe tip 42, extending the probe tip 42 with a small and adjustable amount of pressure, and beginning meridian reading process.

The probe apparatus may also be comprised of an acupressure point finding mode. This mode is initiated when the probe switch 52 is depressed and held down and the probe may stay in this mode until probe switch 52 is released. This mode may be comprised of a sequence of events and or actions including: extending the probe tip 42 and holding it in its extended position with an adjustable amount of pressure, providing meridian readings to the feedback loop, audible, visual and tactile indicators that vary based on the strength of the meridian signal. The motive of the indicators is to aid the practitioner in positioning the probe tip 42 over and aligning the probe tip 42 with an acupressure point.

Figure 7:
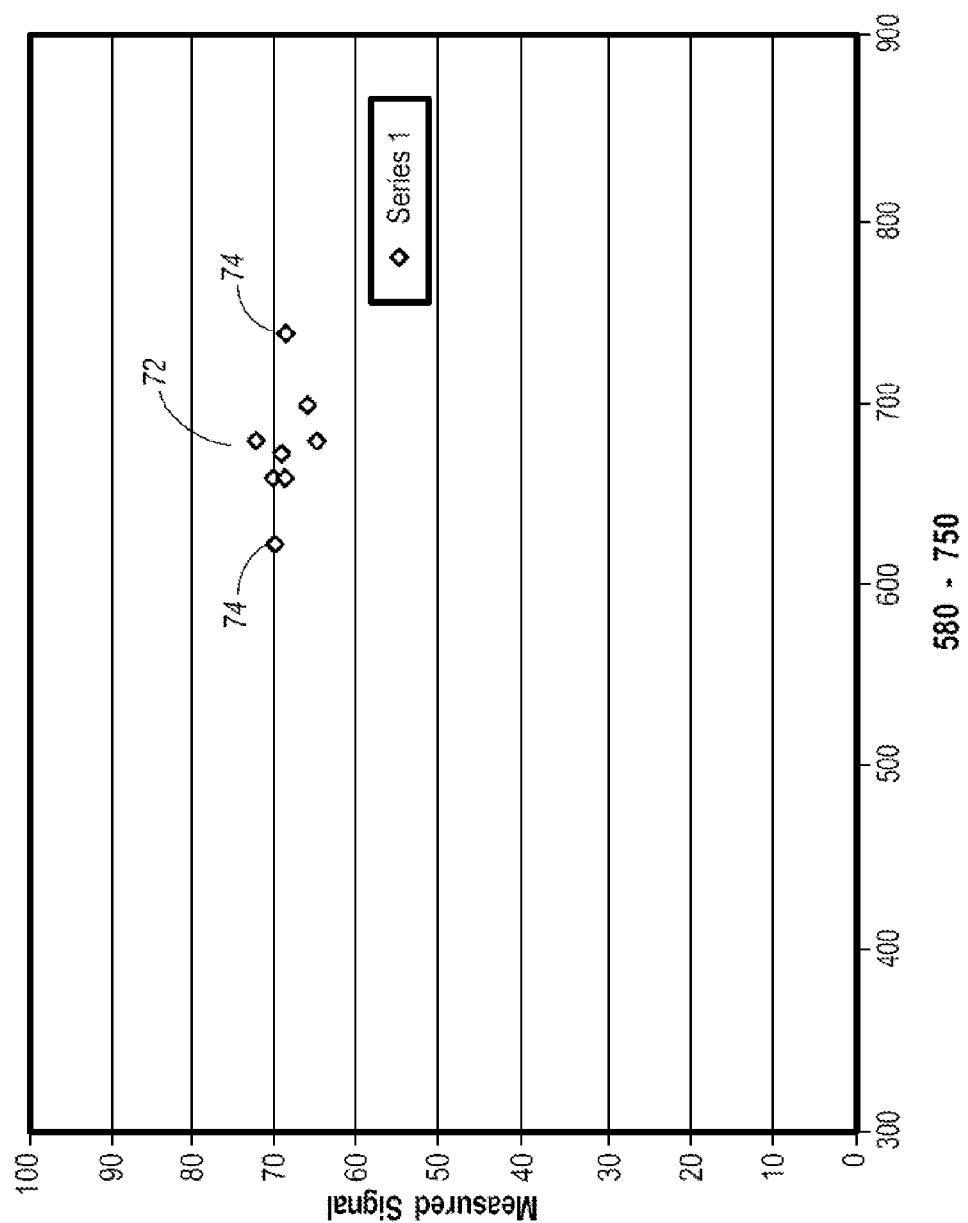
FIG. 7 is a point plot illustrating the consistency of electrical measurements obtained as a result of the present method
Figure 8:
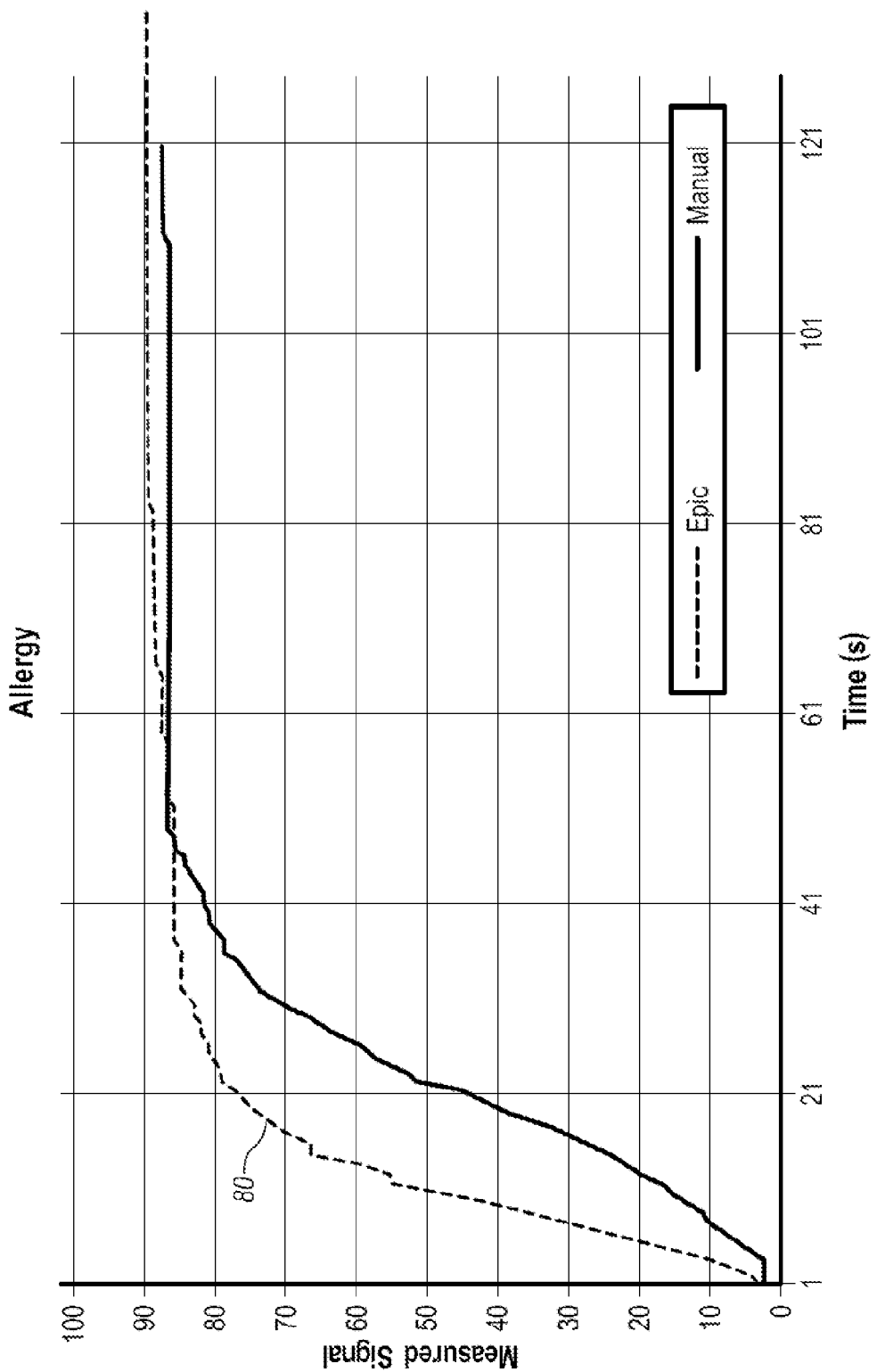
FIGS. 8-12 illustrate additional comparative graphical representations illustrating the efficiency and consistency of the present method ("Epic" in the legends) in obtaining an electrical signal compared to the prior art ("Manual" in the legends)
Figure 9:
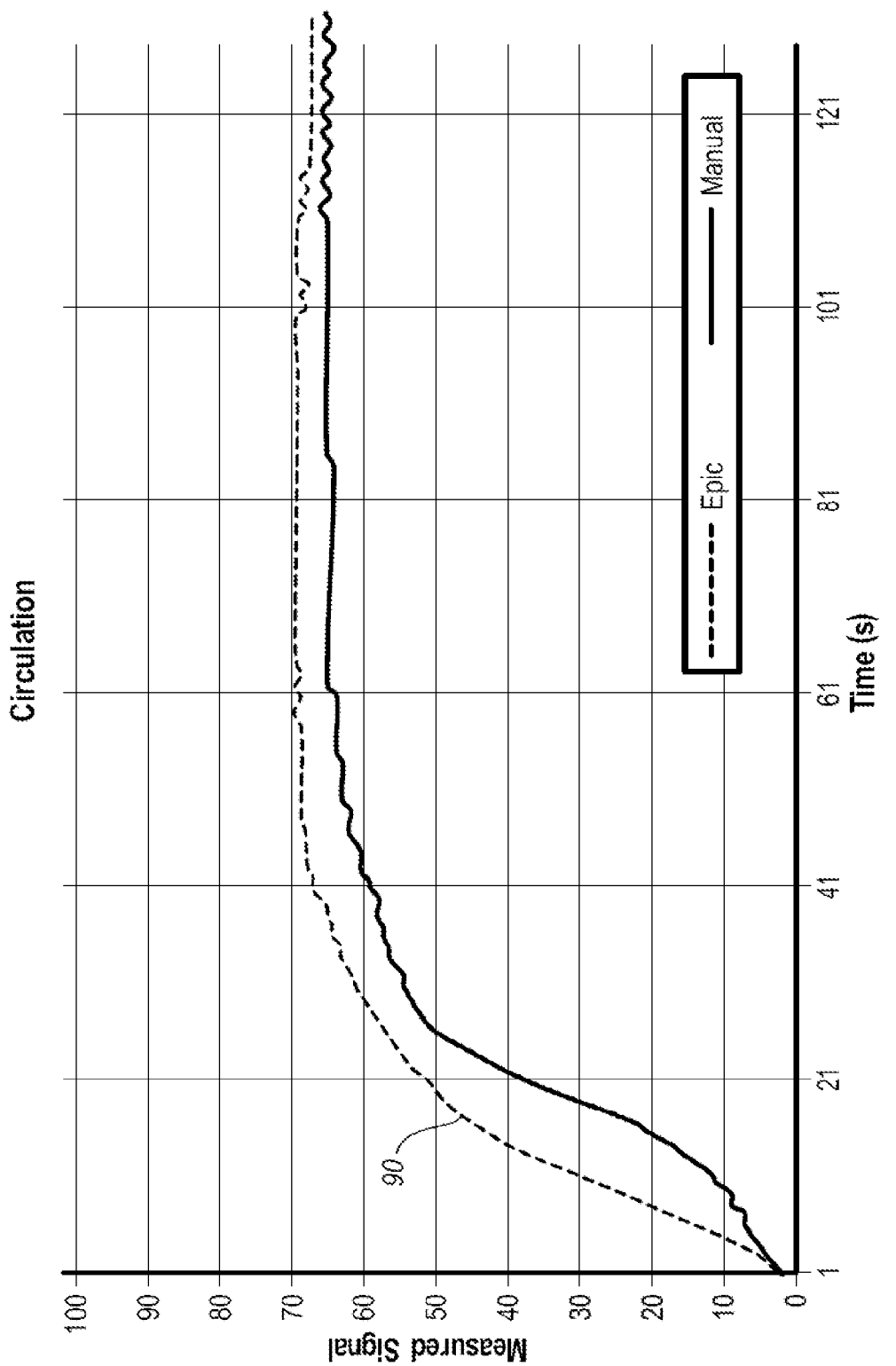
Figure 10:
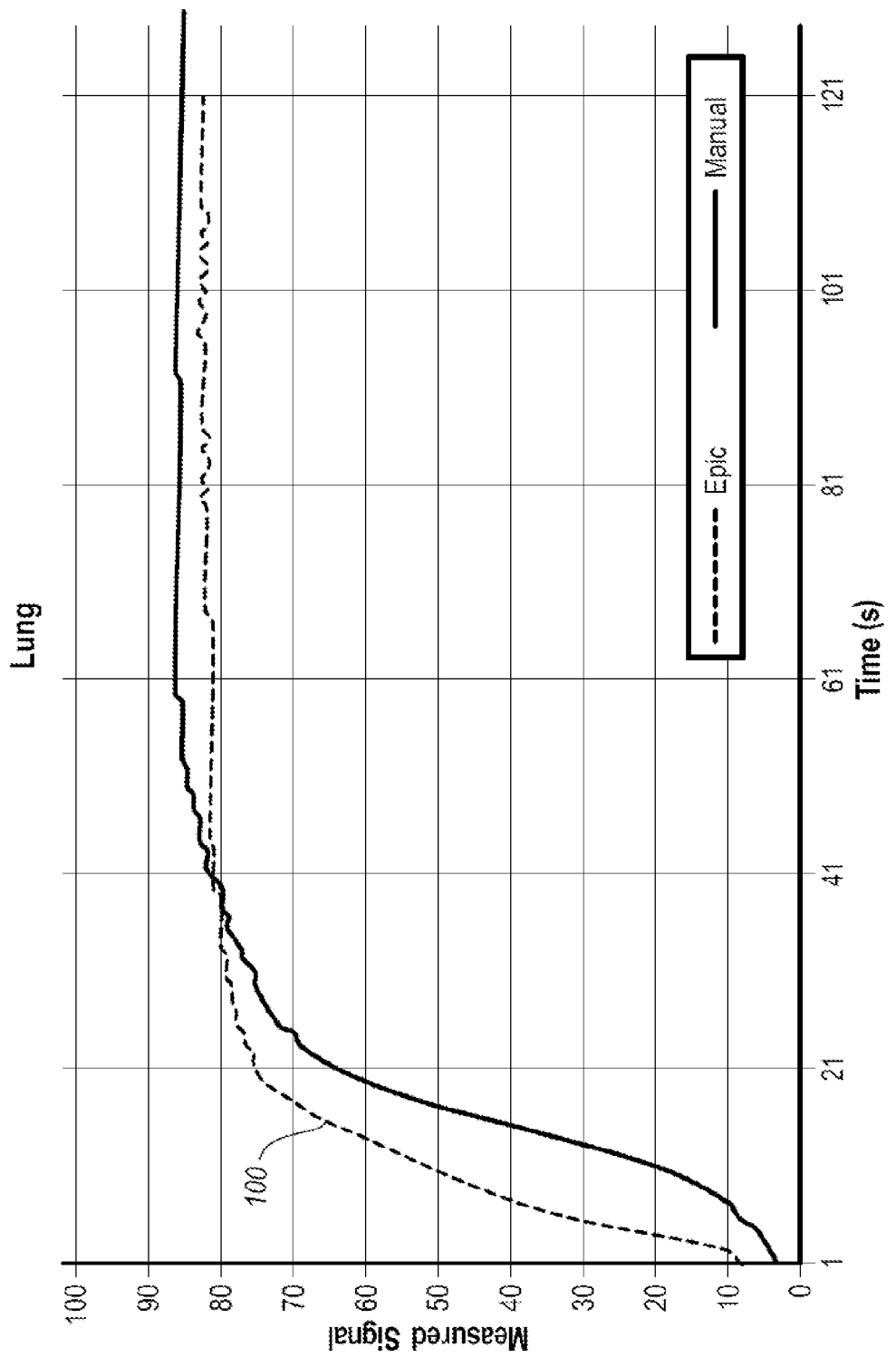
Figure 11:
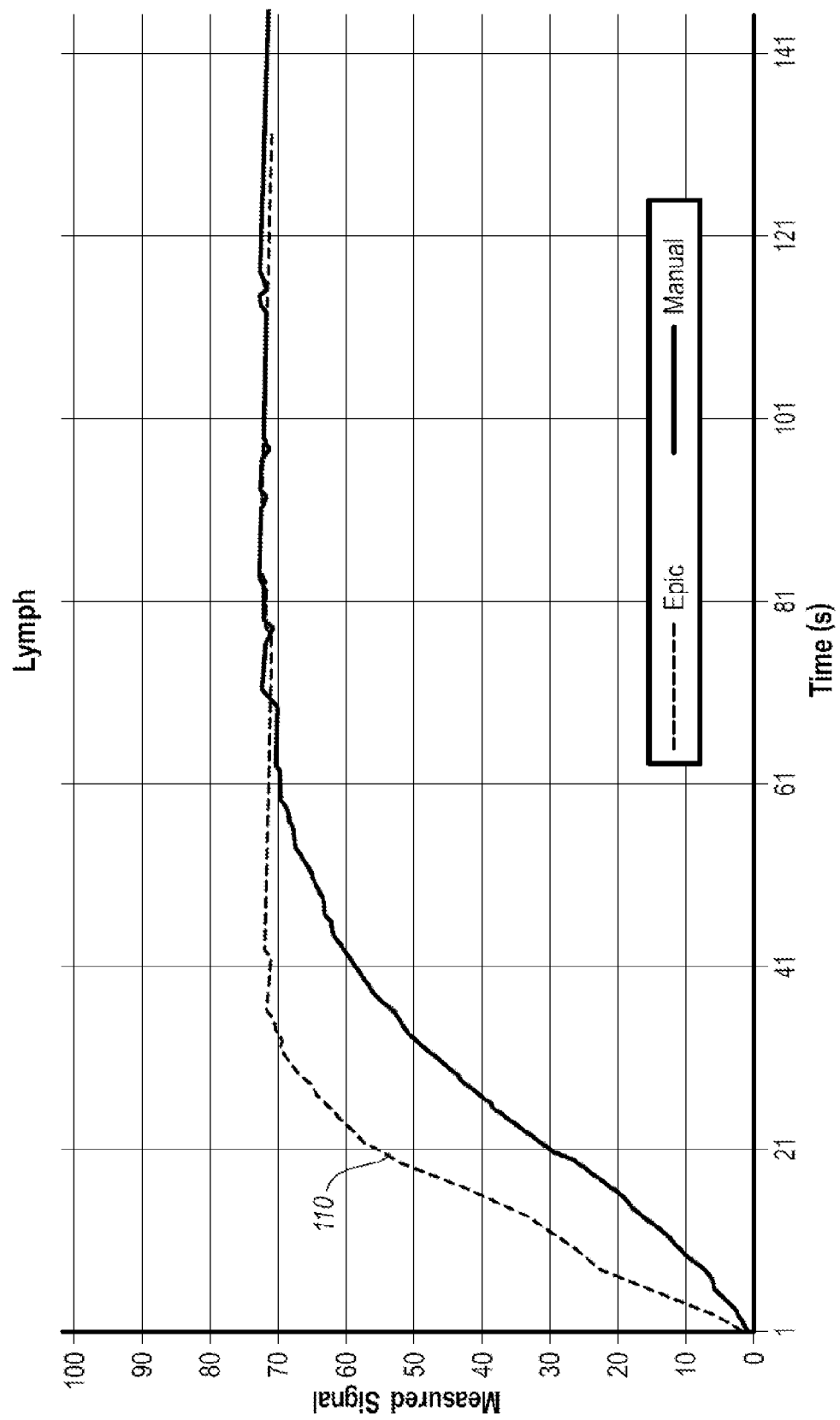
Figure 12:
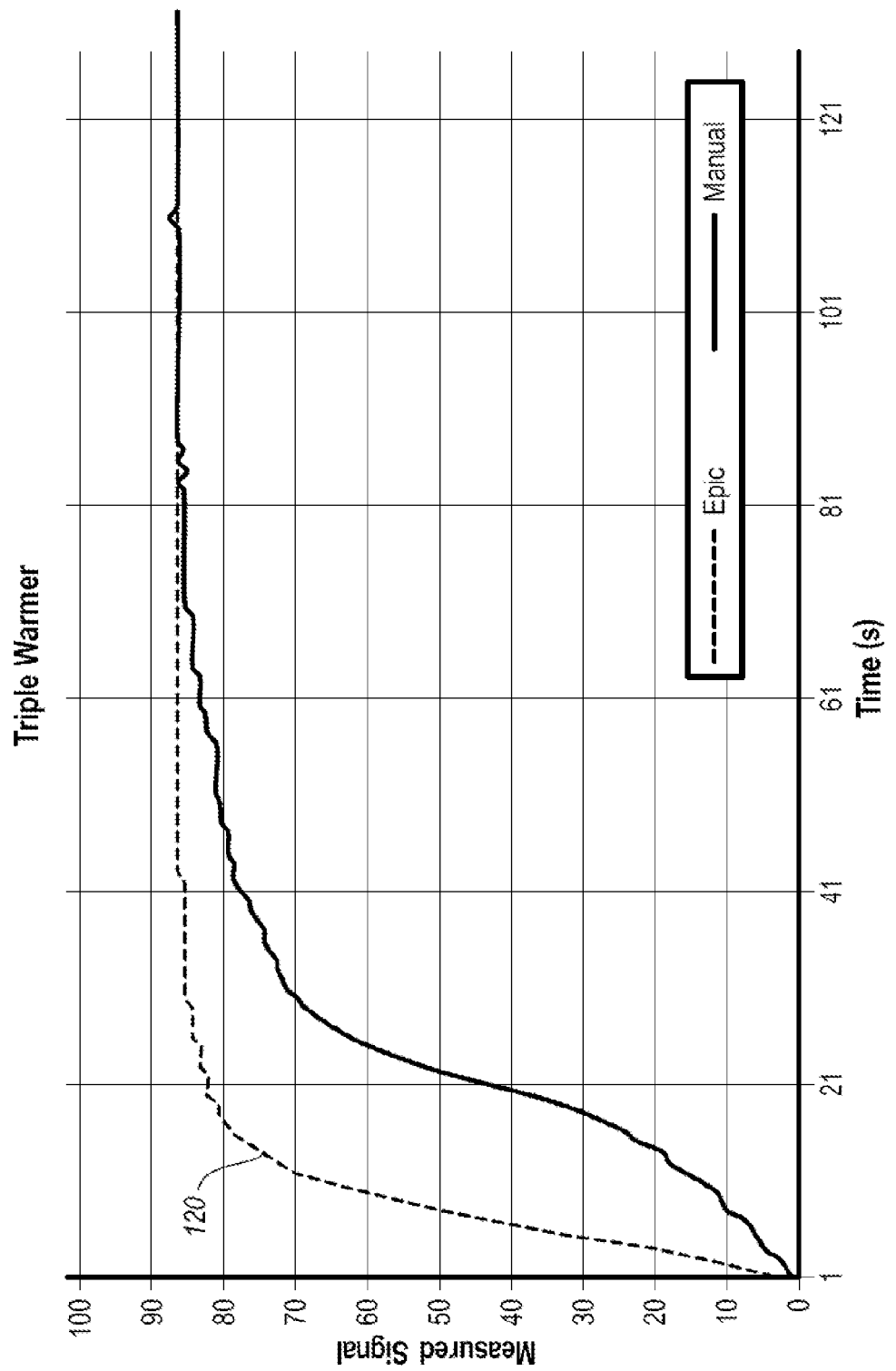

Referring now to FIGS. 6 and 7, utilizing the present method to obtain an electrical signal is both more efficient and more precise than prior art methods. Indeed, prior art methods 62 rely on trial and error in both locating the general dermal area corresponding to a meridian and in applying pressure to such dermal area to obtain an appropriate meridian reading. These methods require considerable time, as evidenced by the prior art rate curve 62, where an accurate electrical signal 70 is obtained considerably later than the same signal obtained through implementation of the present method 68. Further, the present method 60 obtains an electrical signal with far greater precision than prior art methods. This point is emphasized with reference to FIG. 7, where readings obtained through implementation of the present method 60 fall within an extremely small range, with two outliers 74 only moderately displaced from the major cluster of readings 72.

Referring now to FIGS. 8-12, additional comparative graphical representations illustrating the efficiency and consistency of the present method in obtaining an electrical signal compared to the prior art. In FIGS. 8-12, curves 80, 90, 100, 110 and 120 respectively illustrate the results of utilizing an embodiment of the present invention and are compared to results of using a prior art technique. Those skilled in the art will appreciate that in each instance, the results of utilizing an embodiment of the present invention include an increased incline and quicker leveling effect of the curve.

Utilizing Electrical Feedback

As provided above, the present invention relates to a method for obtaining electrical signals from a patient to assess a medical condition. In particular, the present invention relates to a method for accurately locating a meridian transdermally and obtaining a value for an electrical attribute corresponding to such a meridian.

In accordance with at least some embodiments of the present invention, electrical feedback is utilized to obtain quick and repeatable electrical signals in accordance with the present invention. In at least some embodiments, a computer device may be utilized in providing the electrical feedback. Accordingly, FIG. 13 and the corresponding discussion are intended to provide a general description of a suitable operating environment in which the invention may be implemented. One skilled in the art will appreciate that the invention may be practiced in a variety of system configurations.

Embodiments of the present invention embrace one or more computer readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system.

Figure 13:
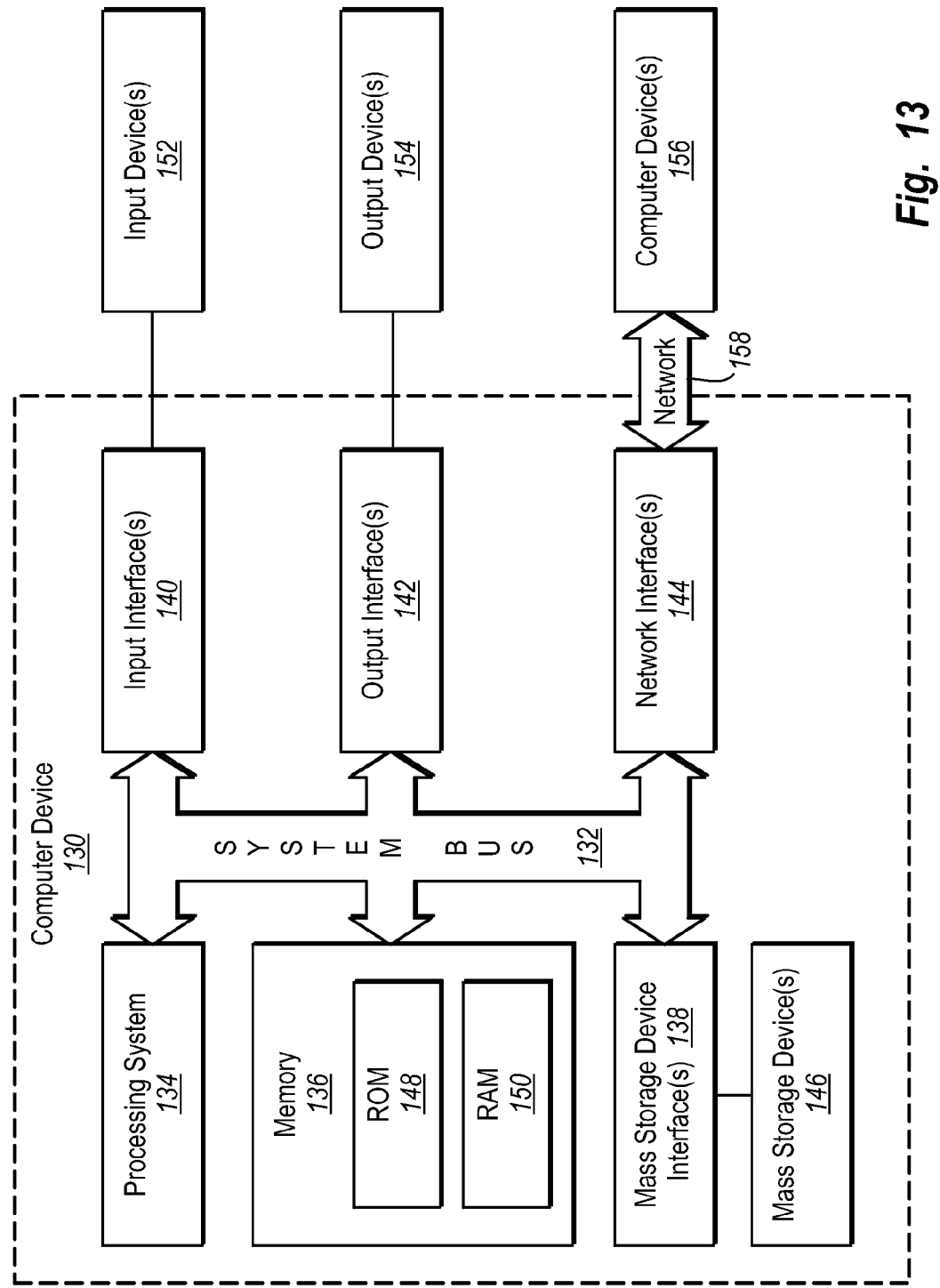
FIG. 13 illustrates a representative system that provides a suitable operating environment for use of electrical methods of the present invention.

With reference to FIG. 13, a representative system for implementing the invention includes computer device 130, which may be a general-purpose or special-purpose computer. For example, computer device 130 may be a personal computer, a notebook computer, a personal digital assistant ("PDA") or other hand-held device, a workstation, a minicomputer, a mainframe, a supercomputer, a multi-processor system, a network computer, a processor-based consumer electronic device, or the like.

Computer device 130 includes system bus 132, which may be configured to connect various components thereof and enables data to be exchanged between two or more components. System bus 132 may include one of a variety of bus structures including a memory bus or memory controller, a peripheral bus, or a local bus that uses any of a variety of bus architectures. Typical components connected by system bus 132 include processing system 134 and memory 136. Other components may include one or more mass storage device interfaces 138, input interfaces 140, output interfaces 142, and/or network interfaces 144, each of which will be discussed below.

Processing system 134 includes one or more processors, such as a central processor and optionally one or more other processors designed to perform a particular function or task. It is typically processing system 134 that executes the instructions provided on computer readable media, such as on memory 136, a magnetic hard disk, a removable magnetic disk, a magnetic cassette, an optical disk, or from a communication connection, which may also be viewed as a computer readable medium.

Memory 136 includes one or more computer readable media that may be configured to include or includes thereon data or instructions for manipulating data, and may be accessed by processing system 134 through system bus 132. Memory 136 may include, for example, ROM 148, used to permanently store information, and/or RAM 150, used to temporarily store information. ROM 148 may include a basic input/output system ("BIOS") having one or more routines that are used to establish communication, such as during start-up of computer device 130. RAM 150 may include one or more program modules, such as one or more operating systems, application programs, and/or program data.

One or more mass storage device interfaces 138 may be used to connect one or more mass storage devices 146 to system bus 132. The mass storage devices 146 may be incorporated into or may be peripheral to computer device 130 and allow computer device 130 to retain large amounts of data. Optionally, one or more of the mass storage devices 146 may be removable from computer device 132. Examples of mass storage devices include hard disk drives, magnetic disk drives, tape drives and optical disk drives. A mass storage device 146 may read from and/or write to a magnetic hard disk, a removable magnetic disk, a magnetic cassette, an optical disk, or another computer readable medium. Mass storage devices 146 and their corresponding computer readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 140 may be employed to enable a user to enter data and/or instructions to computer device 130 through one or more corresponding input devices 152. Examples of such input devices include a keyboard and alternate input devices, such as a mouse, trackball, light pen, stylus, or other pointing device, a microphone, a joystick, a game pad, a satellite dish, a scanner, a camcorder, a digital camera, and the like. Similarly, examples of input interfaces 140 that may be used to connect the input devices 152 to the system bus 132 include a serial port, a parallel port, a game port, a universal serial bus ("USB"), a firewire (IEEE 1394), or another interface.

One or more output interfaces 142 may be employed to connect one or more corresponding output devices 154 to system bus 132. Examples of output devices include a monitor or display screen, a speaker, a printer, and the like. A particular output device 154 may be integrated with or peripheral to computer device 130. Examples of output interfaces include a video adapter, an audio adapter, a parallel port, and the like.

One or more network interfaces 144 enable computer device 130 to exchange information with one or more other local or remote computer devices, illustrated as computer devices 156, via a network 158 that may include hardwired and/or wireless links. Examples of network interfaces include a network adapter for connection to a local area network ("LAN") or a modem, wireless link, or other adapter for connection to a wide area network ("WAN"), such as the Internet. The network interface 144 may be incorporated with or peripheral to computer device 130. In a networked system, accessible program modules or portions thereof may be stored in a remote memory storage device. Furthermore, in a networked system computer device 130 may participate in a distributed computing environment, where functions or tasks are performed by a plurality of networked computer devices.

With reference now to FIG. 14, a flow chart is provided that illustrates a representative embodiment for providing feedback in obtaining quick and repeatable electrical signals. In accordance with at least some embodiments of the present invention, a feedback loop is used to enable the decision on when to stop applying pressure. In accordance with embodiments of the present invention, the rate that the motor is applying pressure is not changed based on the readings. Rather, the pressure stays constant regardless of the readings until the point is reached to not apply any more pressure. And, the electrical feedback loop feeds the decision on when to stop applying pressure. FIG. 14 is a representative embodiment for such methods. In FIG. 14, execution begins at decision block 160 for a determination as to whether or not a reading value of greater than zero is received.

Thus, as discussed herein, the embodiments of the present invention embraces a method for obtaining electrical signals from a patient to assess a medical condition. In particular, the present invention relates to a method for accurately locating a meridian transdermally and obtaining a value for an electrical attribute corresponding to such a meridian. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A method for obtaining an electrical signal from a patient at the patient's skin, said method comprising:
    locating a probe in contact with the patient's skin for measuring an electrical signal of a dermal area, wherein the probe comprises a distally disposed isolation hood and a probe tip configured to independently slide through the isolation hood;
    contacting, with the isolation hood of said probe, the first dermal area;
    actuating a motor and feedback loop to apply pressure to the probe tip independent of the pressure on the isolation hood against the skin; and
    measuring, at the skin, an electrical attribute corresponding to the applied pressure of the probe tip against the dermal area.

2. The method of claim 1, wherein locating a probe for measuring an electrical signal of a dermal area further comprises providing a point locator for indicating a dermal location having a substantially greater electrical signal values than a surrounding dermal area, said point locator configured to produce audible signals indicating said dermal location.

3. The method of claim 1, wherein said probe further comprises:
    a biasing element operably connected to said probe tip to control at least one of the following:
        a) the rate that pressure is applied to said probe tip, and
        b) the amount of pressure applied to said probe tip.

4. The method of claim 1, wherein the biasing element is controlled via a feedback loop to provide a feedback signal containing information with respect to said electrical signal.

5. The method of claim 1, wherein said probe tip further comprises:
    a convex conductive base; and
    an abrasive bristly matrix coupled to a surface area of said convex conductive base, wherein a plurality of bristles of said abrasive bristly matrix simultaneously contact said dermal area.

6. The method of claim 1, wherein said applying pressure to said probe further comprises:
    stabilizing said probe against said dermal area;
    iteratively measuring a electrical signal value of said dermal area as said pressure increases
    iteratively comparing a present electrical signal value of said dermal area corresponding to a present amount of pressure to a previous electrical signal value corresponding to a previous amount of pressure; and;
    changing said future amount of pressure when said present electrical signal value is substantially different than said previous electrical signal value.

7. A method for obtaining an electrical signal from a patient at the patient's skin, said method comprising:
    locating a probe in contact with the patient's skin for measuring an electrical signal of a first dermal area exhibiting higher conductivity than adjacent dermal areas, wherein the probe comprises a distally disposed isolation hood and a probe tip configured to independently slide through the isolation hood;
    contacting, with the isolation hood of said probe, the first dermal area;

actuating a motor and feedback loop to apply pressure to the probe tip independent of the pressure on the isolation hood against the skin; and measuring, at the skin, an electrical attribute corresponding to the applied pressure of the probe tip against said first dermal area.

8. The method of claim 7, wherein locating a probe for measuring an electrical signal of a first dermal area further comprises providing a point locator for indicating a dermal location having a substantially greater electrical signal values than a surrounding dermal area, said point locator configured to produce audible signals indicating said dermal location.

9. The method of claim 7, wherein said probe further comprises:
   a biasing element operably connected to said probe tip to control at least one of the following:
      a) the rate that pressure is applied to said probe tip, and
      b) the amount of pressure applied to said probe tip.

10. The method of claim 7, wherein the biasing element is controlled via a feedback loop to provide a feedback signal containing information with respect to said electrical signal.

11. The method of claim 7, wherein said probe tip further comprises:
   a convex conductive base; and
   an abrasive bristly matrix coupled to a surface area of said convex conductive base, wherein a plurality of bristles of said abrasive bristly matrix simultaneously contact said first dermal area.

12. The method of claim 7, wherein said applying pressure to said probe further comprises:
   stabilizing said probe against said first dermal area;
   iteratively measuring a electrical signal value of said first dermal area as said pressure increases;
   iteratively comparing a present electrical signal value of said first dermal area corresponding to a present amount of pressure to a previous electrical signal value corresponding to a previous amount of pressure; and;
   changing said future amount of pressure when said present electrical signal value is substantially different than said previous electrical signal value.

* * * * *